United States Patent
Merrill et al.

(10) Patent No.: US 6,641,617 B1
(45) Date of Patent: Nov. 4, 2003

(54) RADIATION AND MELT TREATED ULTRA HIGH MOLECULAR WEIGHT POLYETHYLENE PROSTHETIC DEVICE AND METHOD

(75) Inventors: Edward W. Merrill, Belmont, MA (US); William H. Harris, Belmont, MA (US); Murali Jasty, Weston, MA (US); Orhun Muratoglu, Cambridge, MA (US); Charles R. Bragdon, Weymouth, MA (US); Daniel O. O'Connor, East Taunton, MA (US); Premnath Venugopalan, Cambridge, MA (US)

(73) Assignees: The General Hospital Corp., Boston, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/454,123

(22) Filed: Dec. 3, 1999

Related U.S. Application Data

(63) Continuation of application No. 08/726,313, filed on Oct. 2, 1996, now abandoned, which is a continuation-in-part of application No. 08/600,744, filed on Feb. 13, 1996, now Pat. No. 5,879,400.

(51) Int. Cl.⁷ .................................................. A61F 2/32
(52) U.S. Cl. ............................... 623/23.58; 623/22.21
(58) Field of Search ........................... 623/23.58, 18.11, 623/22.11, 22.15, 22.21, 20.14, 20.22

(56) References Cited

U.S. PATENT DOCUMENTS

| | | | |
|---|---|---|---|
| 4,586,995 A | 5/1986 | Randall et al. ................. 522/5 |
| 4,892,552 A * | 1/1990 | Ainsworth et al. ....... 623/23.15 |
| 4,902,460 A | 2/1990 | Yagi et al. ..................... 264/83 |
| 5,001,008 A | 3/1991 | Tokita et al. ............... 428/400 |
| 5,001,206 A | 3/1991 | Bashir et al. ............... 526/352 |
| 5,059,196 A * | 10/1991 | Coates ........................... 606/99 |
| 5,066,755 A | 11/1991 | Lemstra .................... 526/348.1 |
| 5,414,049 A * | 5/1995 | Sun et al. .................. 525/333.7 |
| 5,428,079 A | 6/1995 | Bastiaansen et al. ........ 522/161 |
| 5,684,124 A | 11/1997 | Howard et al. ............. 528/481 |
| 5,753,182 A | 5/1998 | Higgins ........................ 422/23 |
| 5,824,411 A | 10/1998 | Shalaby et al. ............. 428/364 |
| 5,879,400 A * | 3/1999 | Merrill et al. ................. 623/22 |
| 5,972,444 A | 10/1999 | Patel et al. ................. 428/35.2 |
| 6,005,053 A | 12/1999 | Parikh et al. ................ 525/221 |
| 6,017,975 A | 1/2000 | Saum et al. ................. 522/161 |
| 6,165,220 A * | 12/2000 | McKellop et al. ............ 623/18 |
| 6,168,626 B1 | 1/2001 | Hyon et al. .............. 623/18.11 |
| 6,174,934 B1 | 1/2001 | Sun et al. .................... 523/113 |
| 6,184,265 B1 * | 2/2001 | Hamilton et al. ........... 522/189 |
| 6,228,900 B1 * | 5/2001 | Shen et al. .................. 522/153 |
| 6,242,507 B1 | 6/2001 | Saum et al. ................. 522/161 |
| 6,245,276 B1 | 6/2001 | McNulty et al. ............ 264/322 |
| 6,281,264 B1 | 8/2001 | Salovey et al. ............. 523/115 |
| 6,316,158 B1 | 11/2001 | Saum et al. ................. 430/130 |

OTHER PUBLICATIONS

Complaint.
Amended Complaint.
Answer of Defendents Massachusetts Institute of Technology and The General Hospital Corporation to Amended Compliant and Amended Counter Claim.
Reply of Plaintiff, Ambuj D. Sagar, Ph.D., to Amended Counterclaim of Defendents Masachusetts Institute of Technology and The General Hospital Corporation.

* cited by examiner

Primary Examiner—Kevin Shaver
Assistant Examiner—Michael B. Priddy
(74) Attorney, Agent, or Firm—Heller Ehrman White & McAuliffe

(57) ABSTRACT

A medical prosthesis for use within the body which is formed of radiation treated ultra high molecular weight polyethylene having substantially no detectable free radicals, is described. Preferred prostheses exhibit reduced production of particles from the prosthesis during wear of the prosthesis, and are substantially oxidation resistant. Methods of manufacture of such devices and material used therein are also provided.

16 Claims, 3 Drawing Sheets

RADIATION AND MELT TREATED ULTRA HIGH MOLECULAR WEIGHT POLYETHYLENE PROSTHETIC DEVICE AND METHOD

This application is a continuation of U.S. Ser. No. 08/726,313, filed Oct. 2, 1996, now abandoned, which is a continuation in part of U.S. Ser. No. 08/600,744, filed on Feb. 13, 1996, now U.S. Pat. No. 5,879,400. The entire contents of the parent applications are expressly incorporated by reference.

FIELD OF THE INVENTION

The present invention relates to the orthopedic field and the provision of prostheses, such as hip and knee implants, as well as methods of manufacture of such devices and material used therein.

BACKGROUND OF THE INVENTION

The use of synthetic polymers, e.g., ultra high molecular weight polyethylene, with metallic alloys has revolutionized the field of prosthetic implants, e.g., their use in total joint replacements for the hip or knee. Wear of the synthetic polymer against the metal of the articulation, however, can result in severe adverse effects which predominantly manifest after several years. Various studies have concluded that such wear can lead to the liberation of ultrafine particles of polyethylene into the periprosthetic tissues. It has been suggested that the abrasion stretches the chain folded crystallites to form anisotropic fibrillar structures at the articulating surface. The stretched-out fibrils can then rupture, leading to production of submicron sized particles. In response to the progressive ingress of these polyethylene particles between the prosthesis and bone, macrophage-induced resorption of the periprosthetic bone is initiated. The macrophage, often being unable to digest these polyethylene particles, synthesize and release large numbers of cytokines and growth factors which can ultimately result in bone resorption by osteoclasts and monocytes. This osteolysis can contribute to mechanical loosening of the prosthesis components, thereby sometimes requiring revision surgery with its concomitant problems.

SUMMARY OF THE INVENTION

It is an object of the invention to provide an implantable prosthesis device formed at least in part of radiation treated ultra high molecular weight polyethylene (UHMWPE) having no detectable free radicals, so as to reduce production of fine particles from the prosthesis during wear of the prosthesis.

It is another object of the invention to reduce osteolysis and inflammatory reactions resulting from prosthesis implants.

It is yet another object of the invention to provide a prosthesis which can remain implanted within a person for prolonged periods of time.

It is yet another object of the invention to provide improved UHMWPE which can be used in the prostheses of the preceding objects and/or in other fabricated articles.

Still another object of the invention is to provide improved UHMWPE which has a high density of cross-links and no detectable free radicals.

A still further object of the invention is to provide improved UHMWPE which has improved wear resistance.

According to the invention, a medical prosthesis for use within the body which is formed of radiation treated ultra high molecular weight polyethylene (UHMWPE) having substantially no detectable free radicals, is provided. The radiation can be, e.g., gamma or electron radiation. Preferably, the UHMWPE has a cross-linked structure, is substantially not oxidized, is substantially oxidation resistant, and has substantially no chain scission. In certain embodiments, part of the prosthesis is in the form of a cup or tray shaped article having a load bearing surface made of this UHMWPE. This load bearing surface can be in contact with a second part of the prosthesis having a mating load bearing surface of a metallic or ceramic material.

Another aspect of the invention is radiation treated UHMWPE having substantially no detectable free radicals. Preferably, this UHMWPE has a cross-linked structure. Preferably, this UHMWPE is substantially oxidation resistant.

Other aspects of the invention are fabricated articles, e.g., with a load bearing surface, and wear resistant coatings, made from such UHMWPE. One embodiment is where the fabricated article is in the form of a bar stock which is capable of being shaped into articles by conventional methods, e.g., machining.

Yet another aspect of the invention includes a method for making a cross-linked UHMWPE having substantially no detectable free radicals. Conventional UHMWPE having polymeric chains is provided. This UHMWPE is irradiated so as to cross-link said polymeric chains. The UHMWPE is heated above the melting temperature of the UHMWPE so that there are substantially no detectable free radicals in the UHMWPE. The UHMWPE is then cooled to room temperature. In certain embodiments, the cooled UHMWPE is machined and/or sterilized.

One preferred embodiment of this method is called CIR-SM, i.e., cold irradiation and subsequent melting. The UHMWPE that is provided is at room temperature or below room temperature.

Another preferred embodiment of this method is called WIR-SM, i.e., warm irradiation and subsequent melting. The UHMWPE that is provided is pre-heated to a temperature below the melting temperature of the UHMWPE.

Another preferred embodiment of this method is called WIR-AM, i.e., warm irradiation and adiabatic melting. In this embodiment, the UHMWPE that is provided is pre-heated to a temperature below the melting temperature of the UHMWPE, preferably between about 100° C. to below the melting temperature of the UHMWPE. Preferably, the UHMWPE is in an insulating material so as to reduce heat loss from the UHMWPE during processing. The pre-heated UHMWPE is then irradiated to a high enough total dose and at a fast enough dose rate so as to generate enough heat in the polymer to melt substantially all the crystals in the material and thus ensure elimination of substantially all detectable free radicals generated by, e.g., the irradiating step. It is preferred that the irradiating step use electron irradiation so as to generate such adiabatic heating.

Yet another aspect of this invention is the product made in accordance with the above described method.

The invention also features a method of making a medical prosthesis from UHMWPE having substantially no detectable free radicals, the prosthesis resulting in reduced production of particles from the prosthesis during wear of the prosthesis. Radiation treated UHMWPE having no detectable free radicals is provided. A medical prosthesis is formed from this UHMWPE so as to reduce production of particles from the prosthesis during wear of the prosthesis, the UHMWPE forming a load bearing surface of the prosthesis.

Formation of the prosthesis can be accomplished by standard procedures known to those skilled in the art, e.g., machining.

Also provided in this invention is a method of treating a body in need of a medical prosthesis. A shaped prosthesis formed of radiation treated UHMWPE having substantially no detectable free radicals is provided. The prosthesis is applied to the body in need of the prosthesis. The prosthesis reduces production of particles from the prosthesis during wear of the prosthesis. In preferred embodiments, the UHMWPE forms a load bearing surface of the prosthesis.

The above and other objects, features and advantages of the present invention will be better understood from the following specification when read in conjunction with the accompanying drawings.

DETAILED DESCRIPTION

This invention provides a medical prosthesis for use within the body which is formed of radiation treated ultra high molecular weight polyethylene (UHMWPE) which has substantially no detectable free radicals.

Figure 1:
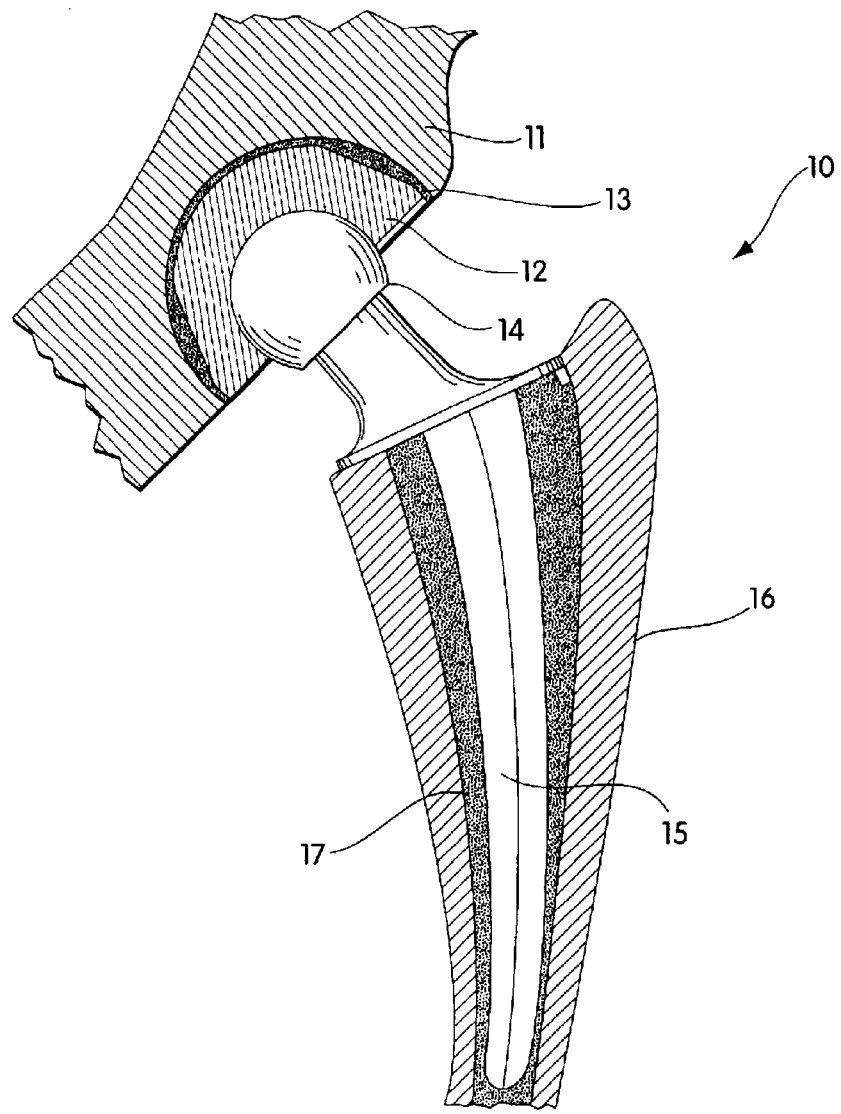
FIG. 1 is a cross-sectional view through the center of a medical hip joint prosthesis in accordance with a preferred embodiment of this invention.

A medical prosthesis in the form of a hip joint prosthesis is generally illustrated at 10 in FIG. 1. The prosthesis shown has a conventional ball head 14 connected by a neck portion to a stem 15 which is mounted by conventional cement 17 to the femur 16. The ball head can be of conventional design and formed of stainless steel or other alloys as known in the art. The radius of the ball head closely conforms to the inner cup radius of an acetabular cup liner 12 which can be mounted in cement 13 directly to the pelvis 11. Alternatively, a metallic acetabular cup can be cemented to the pelvis and the cup liner 12 can form a coating or liner connected to the cup by cement or other means as known in the art.

The specific form of the prosthesis can vary greatly as known in the art. Many hip joint constructions are known and other prostheses such as knee joints, shoulder joints, ankle joints, elbow joints and finger joints are known. All such prior art prostheses can be benefited by making at least one load bearing surface of such prosthesis of a high molecular weight polyethylene material in accordance with this invention. Such load bearing surfaces can be in the form of layers, linings or actual whole devices as shown in FIG. 1. In all cases, it is preferred that the load bearing surface act in conjunction with a metallic or ceramic mating member of the prosthesis so that a sliding surface is formed therebetween. Such sliding surfaces are subject to breakdown of the polyethylene as known in the prior art. Such breakdown can be greatly diminished by use of the materials of the present invention.

Figure 2:
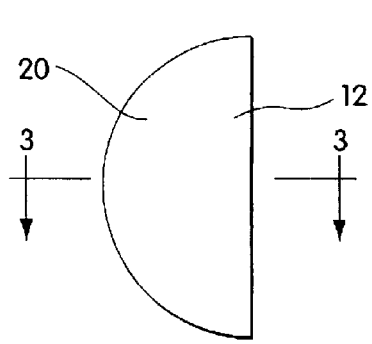
FIG. 2 is a side view of an acetabular cup liner as shown in FIG. 1.
Figure 3:
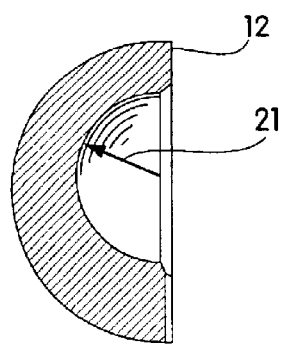
FIG. 3 is a cross-sectional view through line 3—3 of FIG. 2.

FIG. 2 shows the cup liner in the form of a half hollow ball-shaped device better seen in the cross-section of FIG. 3. As previously described, the outer surface 20 of the cup liner need not be circular or hemispherical but can be square or of any configuration to be adhered directly to the pelvis or to the pelvis through a metallic cup as known in the art. The radius of the cup liner shown at 21 in FIG. 3 of the preferred embodiment ranges from about 20 mm to about 35 mm. The thickness of the cup liner from its generally hemispherical hollow portion to the outer surface 20 is preferably about 8 mm. The outer radius is preferably in the order of about 20 mm to about 35 mm.

In some cases, the ball joint can be made of the UHMWPE of this invention and the cup formed of metal, although it is preferred to make the cup or cup liner of UHMWPE to mate with the metallic ball. The particular method of attachment of the components of the prosthesis to the bones of the body can vary greatly as known in the art.

The medical prosthesis includes, e.g., orthopedic joint and bone replacement parts, e.g., hip, knee, shoulder, elbow, ankle or finger replacements. The prosthesis can be in the form, e.g., of a cup or tray shaped article which has a load bearing surface. Other forms known to those skilled in the art are also included in the invention. Medical prostheses are also meant to include any wearing surface of a prosthesis, e.g., a coating on a surface of a prosthesis in which the prosthesis is made from a material other than the UHMWPE of this invention.

The prostheses of this invention are useful for contact with metal containing parts formed of, e.g., stainless steel, titanium alloy or nickel cobalt alloy, or with ceramic containing parts. For example, a hip joint is constructed in which a cup shaped article having an inner radius of 25 mm, is contacted with a metal ball having an outer radius of 25 mm, so as to closely mate with the cup shaped article. The load bearing surface of the cup shaped article of this example is made from the UHMWPE of this invention, preferably having a thickness of at least about 1 mm, more preferably having a thickness of at least about 2 mm, more preferably having a thickness of at least about ¼ inch, and more preferably yet having a thickness of at least about ⅓ inch.

The prostheses can have any standard known form, shape, or configuration, or be a custom design, but have at least one load bearing surface of UHMWPE of this invention.

The prostheses of this invention are non-toxic to humans. They are not subject to deterioration by normal body constituents, e.g., blood or interstitial fluids. They are capable of being sterilized by standard means, including, e.g., heat or ethylene oxide.

By UHMWPE is meant linear non-branched chains of ethylene that have molecular weights in excess of about 500,000, preferably above about 1,000,000, and more preferably above about 2,000,000. Often the molecular weights can reach about 8,000,000. By initial average molecular weight is meant the average molecular weight of the UHMWPE starting material, prior to any irradiation.

By radiation treated UHMWPE is meant UHMWPE which has been treated with radiation, e.g., gamma radiation or electron radiation, so as to induce cross-links between the polymeric chains of the UHMWPE.

By substantially no detectable free radicals is meant substantially no free radicals as measured by electron paramagnetic resonance, as described in Jahan et al., J. Biomedical Materials Research 25:1005 (1991). Free radicals include, e.g., unsaturated trans-vinylene free radicals. UHMWPE that has been irradiated below its melting point with ionizing radiation contains cross-links as well as long-lived trapped free radicals. These free radicals react with oxygen over the long-term and result in the embrittlement of the UHMWPE through oxidative degradation. An advantage of the UHMWPE and medical prostheses of this invention is that radiation treated UHMWPE is used which has no detectable free radicals. The free radicals can be eliminated by any method which gives this result, e.g., by heating the UHMWPE above its melting point such that substantially no residual crystalline structure remains. By eliminating the crystalline structure, the free radicals are able to recombine and thus are eliminated.

Preferably, the UHMWPE which is used in this invention has a cross-linked structure. An advantage of having a cross-linked structure is that it will reduce production of particles from the prosthesis during wear of the prosthesis.

It is preferred that the UHMWPE be substantially not oxidized. By substantially not oxidized is meant that the ratio of the area under the carbonyl peak at 1740 $cm^{-1}$ in the FTIR spectra to the area under the peak at 1460 $cm^{-1}$ in the FTIR spectra of the cross-linked sample be of the same order of magnitude as the ratio for the sample before cross-linking.

It is preferred that the UHMWPE be substantially oxidation resistant. By substantially oxidation resistant is meant that it remains substantially not oxidized for at least about 10 years. Preferably, it remains substantially not oxidized for at least about 20 years, more preferably for at least about 30 years, more preferably yet for at least about 40 years, and most preferably for the entire lifetime of the patient.

It is preferred that the UHMWPE have substantially no chain scission. By substantially no chain scission is meant that the fraction of the polymer sample dissolving in normal xylene at 130° C. or decalin at 150° C. and remaining in solution after cooling to room temperature be less than or equal to the fraction of the conventional UHMWPE dissolving in normal xylene at 130° C. or decalin at 150° C. and remaining in solution after cooling to room temperature within the margins of experimental error. In some embodiments, the polymeric structure has extensive cross-linking such that a substantial portion of the polymeric structure does not dissolve in xylene or decalin. By substantial portion is meant at least 50% of the polymer sample's dry weight. By not dissolve in xylene or decalin is meant does not dissolve in xylene at 130° C. or decalin at 150° C. over a period of 24 hours.

The polymeric structure of the UHMWPE used in the prostheses of this invention results in the reduction of production of UHMWPE particles from the prosthesis during wear of the prosthesis. As a result of the limited number of particles being shed into the body, the prosthesis exhibits longer implant life. Preferably, the prosthesis can remain implanted in the body for at least 10 years, more preferably for at least 20 years and most preferably for the entire lifetime of the patient.

The invention also includes other fabricated articles made from radiation treated UHMWPE having substantially no detectable free radicals. Preferably, the UHMWPE which is used for making the fabricated articles has a cross-linked structure. Preferably, the UHMWPE is substantially oxidation resistant. Such articles include shaped articles and unshaped articles, including, e.g., machined or molded objects, e.g., cups, gears, nuts, sled runners, bolts, fasteners, cables and the like, and bar stock, films, cylindrical bars, sheeting, panels, and fibers. Shaped articles can be made, e.g., by machining. The fabricated articles are particularly suitable for load bearing applications, e.g., as a load bearing surface, and as metal replacement articles. Thin films or sheets of the UHMWPE of this invention can also be attached, e.g., with glue, onto supporting surfaces, and thus used as a wear resistant load bearing surface.

The invention also includes radiation treated UHMWPE which has substantially no detectable free radicals. Preferably, the UHMWPE has a cross-linked structure. Preferably, the UHMWPE is substantially oxidation resistant. Depending upon the particular processing used to make the UHMWPE, certain impurities may be present in the UHMWPE of this invention, including, e.g., calcium stearate, mold release agents, extenders, anti-oxidants and/or other conventional additives to polyethylene polymers.

The invention also provides a method for making cross-linked UHMWPE having substantially no detectable free radicals. Preferably, this UHMWPE is for use as a load bearing article. Conventional UHMWPE having polymeric chains is provided. The conventional UHMWPE can be in the form of, e.g., a bar stock, a shaped bar stock, a coating, or a fabricated article, e.g., a cup or tray shaped article for use in a medical prosthesis. By conventional UHMWPE is meant commercially available high density (linear) polyethylene of molecular weights greater than about 500,000. Preferably, the UHMWPE starting material has an average molecular weight of greater than about 2 million. By initial average molecular weight is meant the average molecular weight of the UHMWPE starting material, prior to any irradiation. The UHMWPE is irradiated so as to cross-link the polymeric chains. The irradiation can be done in an inert or non-inert environment. Preferably, the irradiation is done in a non-inert environment, e.g., air. The irradiated UHMWPE is heated above the melting temperature of the UHMWPE so that there are substantially no detectable free radicals in the UHMWPE. The heated UHMWPE is then cooled to room temperature. Preferably, the cooling step is at a rate greater than about 0.1° C./minute. Optionally, the cooled UHMWPE can be machined. For example, if any oxidation of the UHMWPE occurred during the irradiating step, it can be machined away if desired, by any method known to those skilled in the art. And optionally, the cooled UHMWPE, or the machined UHMWPE, can be sterilized by any method known to those skilled in the art.

One preferred embodiment of this method is called CIR-SM, i.e., cold irradiation and subsequent melting. In this embodiment, the UHMWPE that is provided is at room temperature or below room temperature. Preferably, it is at room temperature. Irradiation of the UHMWPE can be with, e.g., gamma irradiation or electron irradiation. In general, gamma irradiation gives a high penetration depth but takes a longer time, resulting in increased cost of operation and the possibility of more in-depth oxidation. In general, electron irradiation gives more limited penetration depths but takes a shorter time, and hence the cost and the possibility of extensive oxidation is reduced. The irradiation is done so as to cross-link the polymeric chains. The irradiation dose can be varied to control the degree of cross-linking and crystallinity in the final UHMWPE product. Preferably, the total absorbed dose of the irradiation is about 0.5 to about 1,000 Mrad, more preferably about 1 to about 100 Mrad, more preferably yet about 4 to about 30 Mrad, and most preferably about 20 Mrad. Preferably, a dose rate is used that does not generate enough heat to melt the UHMWPE. If gamma irradiation is used, the preferred dose rate is about 0.05 to about 0.2 Mrad/minute. If electron irradiation is used, preferably the dose rate is about 0.05 to about 3,000 Mrad/minute, more preferably about 0.05 to about 5 Mrad/minute, and most preferably about 0.05 to about 0.2 Mrad/minute. When electron irradiation is used, the energy of the electrons can be varied to change the depth of penetration of the electrons. Preferably, the energy of the electrons is about 0.5 MeV to about 12 MeV, more preferably about 5 MeV to about 12 MeV. Such manipulability is particularly useful when the irradiated object is an article of varying thickness or depth, e.g., an articular cup for a medical prosthesis.

The irradiated UHMWPE is heated above the melting temperature of the UHMWPE so that there are no detectable free radicals in the UHMWPE. The heating provides the molecules with sufficient mobility so as to eliminate the constraints derived from the crystals of the UHMWPE, thereby allowing essentially all of the residual free radicals to recombine. Preferably, the UHMWPE is heated to a temperature of about 137° C. to about 300° C., more preferably about 140° C. to about 300° C., more preferably yet about 140° C. to about 190° C., and most preferably about 150° C. Preferably, the temperature in the heating step is maintained for about 0.5 minutes to about 24 hours, more preferably about 1 hour to about 3 hours, and most preferably about 2 hours. The heating can be carried out, e.g., in air, in an inert gas, e.g., nitrogen, argon or helium, in a sensitizing atmosphere, e.g., acetylene, or in a vacuum. It is preferred that for the longer heating times, that the heating be carried out in an inert gas or under vacuum.

Another preferred embodiment of this method is called WIR-SM, i.e., warm irradiation and subsequent melting. In this embodiment, the UHMWPE that is provided is pre-heated to a temperature below the melting temperature of the UHMWPE. The pre-heating can be done in an inert or non-inert environment. It is preferred that this pre-heating is done in air. Preferably, the UHMWPE is pre-heated to a temperature of about 20° C. to about 135° C.; more preferably the temperature is about 50° C. The other parameters are as described above for the CIR-SM embodiment, except that the dose rate for the irradiating step preferably is about 0.05 to about 10 Mrad/minute, and more preferably is about 4 to about 5 Mrad/minute.

Another preferred embodiment of this method is called WIR-AM, i.e., warm irradiation and adiabatic melting. In this embodiment, the UHMWPE that is provided is pre-heated to a temperature below the melting temperature of the UHMWPE. The pre-heating can be done in an inert or non-inert environment. It is preferred that this pre-heating is done in air. The pre-heating can be done, e.g., in an oven. It is preferred that the pre-heating is to a temperature between about 100° C. to below the melting temperature of the UHMWPE. Preferably, the UHMWPE is pre-heated to a temperature of about 100° C. to about 135° C., more preferably the temperature is about 130° C. Preferably, the UHMWPE is in an insulating material so as to reduce heat loss from the UHMWPE during processing. The heat is meant to include, e.g., the pre-heat delivered before irradiation and the heat generated during irradiation. By insulating material is meant any type of material which has insulating properties, e.g., a fiberglass pouch.

The pre-heated UHMWPE is then irradiated to a high enough total dose and at a fast enough dose rate so as to generate enough heat in the polymer to melt substantially all the crystals in the material and thus ensure elimination of substantially all detectable free radicals generated by, e.g., the irradiating step. It is preferred that the irradiating step use electron irradiation so as to generate such adiabatic heating. The minimum total dose is determined by the amount of heat necessary to heat the polymer from its initial temperature (i.e., the pre-heated temperature discussed above) to its melting temperature, and the heat necessary to melt all the crystals, and the heat necessary to heat the polymer to a pre-determined temperature above its melting point. The following equation describes how the amount of total dose is calculated:

$$\text{Total Dose} = c_{p_s}(T_m - T_i) + \Delta H_m + c_{p_m}(T_f - T_m)$$

where $c_{p_s}$ (=2 J/g/° C.=2 kGy/° C.=0.2 Mrad/° C.) and $c_{p_m}$ (=3 J/g/° C.=3 kGy° C.=0.3 Mrad/°C.) are heat capacities of UHMWPE in the solid state and melt state, respectively, $\Delta H_m$ (=146 J=14.6 Mrad for GUR 415 bar stock) is the heat of melting of the unirradiated polymer, $T_i$ is the initial temperature, and $T_f$ is the final temperature. The final temperature should be above the melting temperature of the UHMWPE.

Preferably, the final temperature of the UHMWPE is about 140° C. to about 200° C., more preferably it is abo or decalin at 150° C. or decalin at 150° C. or decalin at 150° C. or decalin at 150° C. ut 150° C. At above 160° C., the polymer starts to form bubbles and cracks. Preferably, the dose rate of the electron irradiation is about 2 to about 3,000 Mrad/minute, more preferably is about 7 to about 25 Mrad/minute, and most preferably is about 20 Mrad/minute. Preferably, the total absorbed dose is about 1 to about 100 Mrad. Using the above equation, the absorbed dose for an initial temperature of 130° C. and a final temperature of 150° C. is calculated to be about 22 Mrad.

In this embodiment, the heating step of the method is the adiabatic heating described above. In certain other embodiments, the method has a second heating step after the adiabatic heating so that the final temperature after the second heating step is above the melting temperature of the UHMWPE.

This invention also includes the product made in accordance with the above described method.

Also provided in this invention is a method of making a medical prosthesis from UHMWPE having substantially no detectable free radicals, the prosthesis resulting in the reduced production of particles from the prosthesis during wear of the prosthesis. Radiation treated UHMWPE having no detectable free radicals is provided. A medical prosthesis is formed from this UHMWPE so as to reduce production of particles from the prosthesis during wear of the prosthesis, the UHMWPE forming a load bearing surface of the prosthesis. Formation of the prosthesis can be accomplished by standard procedures known to those skilled in the art, e.g., machining.

Also provided in this invention is a method of treating a body in need of a medical prosthesis. A shaped prosthesis formed of radiation treated UHMWPE having substantially no detectable free radicals is provided. This prosthesis is applied to the body in need of the prosthesis. The prosthesis reduces production of fine particles from the prosthesis during wear of the prosthesis. In preferred embodiments, the ultra high molecular weight polyethylene forms a load bearing surface of the prosthesis.

In yet another embodiment of this invention, a medical prosthesis for use within the body which is formed of ultra high molecular weight polyethylene (UHMWPE) which has a polymeric structure with less than about 50% crystallinity, less than about 290 Å lamellar thickness and less than about 940 MPa tensile elastic modulus, so as to reduce production of fine particles from the prosthesis during wear of the prosthesis, is provided.

The UHMWPE of this embodiment has a polymeric structure with less than about 50% crystallinity, preferably less than about 40% crystallinity, more preferably less than about 35% crystallinity, and most preferably less than about 30% crystallinity. By crystallinity is meant the fraction of the polymer that is crystalline. The crystallinity is calculated by knowing the weight of the sample (w, in g), the heat absorbed by the sample in melting (E, in cal) and the heat of melting of polyethylene crystals (ΔH=69.2 cal/g), and using the following equation:

$$\% \text{ crystallinity} = \frac{E}{w \cdot \Delta H}$$

The UHMWPE of this embodiment has a polymeric structure with less than about 290 Å lamellar thickness, preferably less than about 200 Å lamellar thickness, and most preferably less than about 100 Å lamellar thickness. By lamellar thickness (l) is meant the calculated thickness of assumed lamellar structures in the polymer using the following expression:

$$l = \frac{2 \cdot \sigma_e \cdot T_m^o}{\Delta H \cdot (T_m^o - T_m) \cdot \rho}$$

where, $\sigma_e$ is the end free surface energy of polyethylene ($2.22 \times 10^{-6}$ cal/cm$^2$), ΔH is the heat of melting of polyethylene crystals (69.2 cal/g), $\rho$ is the density of the crystalline regions (1.005 g/cm$^3$), $T_m^o$ is the melting point of a perfect polyethylene crystal (418.15K) and $T_m$ is the experimentally determined melting point of the sample.

The UHMWPE of this embodiment has less than about 940 MPa tensile elastic modulus, preferably less than about 600 MPa tensile elastic modulus, more preferably less than about 400 MPa tensile elastic modulus, and most preferably less than about 200 MPa tensile elastic modulus. By tensile elastic modulus is meant the ratio of the nominal stress to corresponding strain for strains less than 0.5% as determined using the standard test ASTM 638 M III.

Preferably, the UHMWPE of this embodiment has a polymeric structure with about 40% crystallinity, about 100 Å lamellar thickness and about 200 MPa tensile elastic modulus.

It is preferred that the UHMWPE of this embodiment have no trapped free radicals, especially unsaturated trans-vinylene free radicals. It is preferred that the UHMWPE of this embodiment have a hardness less than about 65 on the Shore D scale, more preferably a hardness less than about 55 on the Shore D scale, most preferably a hardness less than about 50 on the. Shore D scale. By hardness is meant the instantaneous indentation hardness measured on the Shore D scale using a durometer described in ASTM D2240. It is preferred that the UHMWPE of this embodiment be substantially not oxidized and/or have substantially no chain scission. In some embodiments, the polymeric structure has extensive cross-linking such that a substantial portion of the polymeric structure does not dissolve in Decalin. By substantial portion is meant at least 50% of the polymer sample's dry weight. By not dissolve in Decalin is meant does not dissolve in Decalin at 150° C. over a period of 24 hours. Preferably, the UHMWPE of this embodiment has a high density of entanglement so as to cause the formation of imperfect crystals and reduce crystallinity. By the density of entanglement is meant the number of points of entanglement of polymer chains in a unit volume; a higher density of entanglement being indicated by the polymer sample's inability to crystallize to the same extent as conventional UHMWPE, thus leading to a lesser degree of crystallinity.

The invention also includes other fabricated articles made from the UHMWPE of this embodiment having a polymeric structure with less than about 50% crystallinity, less than about 290 Å lamellar thickness and less than about 940 MPa tensile elastic modulus. Such articles include shaped articles and unshaped articles, including, e.g., machined or molded objects, e.g., cups, gears, nuts, sled runners, bolts, fasteners, cables and the like, and bar stock, films, cylindrical bars, sheeting, panels, and fibers. Shaped articles can be made, e.g., by machining. The fabricated articles are particularly suitable for load bearing applications, e.g., as a load bearing surface, and as metal replacement articles. Thin films or sheets of UHMWPE, which have been melt-irradiated can also be attached, e.g., with glue, onto supporting surfaces, and thus used as a transparent, wear resistant load bearing surface.

The invention also includes an embodiment in which UHMWPE has a unique polymeric structure characterized by less than about 50% crystallinity, less than about 290 Å lamellar thickness and less than about 940 MPa tensile elastic modulus. Depending upon the particular processing used to make the UHMWPE, certain impurities may be present in the UHMWPE of this invention, including, e.g., calcium stearate, mold release agents, extenders, anti-oxidants and/or other conventional additives to polyethylene polymers. In certain embodiments, the UHMWPE has high transmissivity of light, preferably a transmission greater than about 10% of light at 517 nm through a 1 mm thick sample, more preferably a transmission greater than about 30% of light at 517 nm through a 1 mm thick sample, and most preferably a transmission greater than about 40% of light at 517 nm through a 1 mm thick sample. Such UHMWPE is particularly useful for thin films or sheets which can be attached onto supporting surfaces of various articles, the film or sheet being transparent and wear resistant.

In another embodiment of this invention, a method for making UHMWPE which is highly entangled and crosslinked is provided. This method is called melt irradiation (MIR). Preferably, this UHMWPE has a polymeric structure with less than about 50% crystallinity, less than about 290 Å lamellar thickness and less than about 940 MPa tensile elastic modulus. Conventional UHMWPE, e.g., a powder, a bar stock, a shaped bar stock, a coating, or a fabricated article is provided. By conventional UHMWPE is meant commercially available high density (linear) polyethylene of molecular weights greater than about 500,000. Preferably, the UHMWPE starting material has an average molecular weight of greater than about 2 million. By initial average molecular weight is meant the average molecular weight of the UHMWPE starting material, prior to any irradiation. This UHMWPE is surrounded with an inert material that is substantially free of oxygen, e.g., nitrogen, argon or helium. The UHMWPE is heated above its melting temperature for a time sufficient to allow the UHMWPE chains to take up an entangled state. Preferably, the temperature is about 145° C. to about 230° C., and more preferably, is about 175° to about 200° C. The period of time of heating should be sufficient to permit the UHMWPE polymer chains to take up a random coil conformation.

Preferably, the heating is maintained so to keep the polymer at the preferred temperature for about 5 minutes to about 3 hours, and more preferably for about 30 minutes to about 2 hours. The UHMWPE is then irradiated so as to trap the polymer chains in the entangled state, e.g., with gamma irradiation or electron irradiation. In general, gamma irradiation gives a high penetration depth but takes a longer time, resulting in increased cost of operation and the possibility of some oxidation. In general, electron irradiation gives more limited penetration depths but takes a shorter time, and hence the cost and the possibility of oxidation is reduced. The irradiation dose can be varied to control the degree of crosslinking and crystallinity in the final UHMWPE product. Preferably, a dose of greater than about 1 MRad is used, more preferably a dose of greater than about 20 MRad is used. When electron irradiation is used, the energy of the electrons can be varied to change the depth of penetration of the electrons, thereby controlling the degree of crosslinking and crystallinity in the final UHMWPE product. Preferably, the energy is about 0.5 MeV to about 10 MeV, more preferably about 1 MeV to about 5 MeV. Such manipulability is particularly useful when the irradiated object is an article of varying thickness or depth, e.g., an articular cup for a prosthesis. The irradiated UHMWPE is then cooled to about 25° C. so as to produce UHMWPE with lower crystallinity than the starting material. Faster cooling rates are preferred. Preferably, the cooling rate is equal to or greater than about 0.5° C./min, more preferably equal to or greater than about 120° C./min. In certain embodiments, the cooled UHMWPE can be machined. Examples 1, 3 and 6 describe preferred embodiments of the method. Examples 2, 4 and 5, and FIGS. 4 through 7, illustrate certain properties of the melt-irradiated UHMWPE obtained from these preferred embodiments, as compared to conventional UHMWPE.

Conventional UHMWPE is standardly generated by Ziegler-Natta catalysis, and as the polymer chains are generated from the surface catalytic site, they crystallize, and interlock as crystal folded chains. Examples of known UHMWPE include Hifax Grade 1900 polyethylene (obtained from Himont USA Corp., Wilmington, Del.) and Hoechst-Celanese GUR-415 polyethylene (obtained from Hoechst-Celanese Corp., Houston, Tex.). Without being bound by any theory, it is believed that if this UHMWPE is subjected to temperatures above the melting point ($T_m$ approximately 135° C.), and if given enough time to relax, each UHMWPE chain should adopt the unperturbed random walk conformation which should lead to enormous chain entanglement. Irradiating the melted UHMWPE should trap the polymers in this entangled state. Upon cooling below the melting point, these entangled chains should, be limited in their ability to crystallize by chain folding. The crystallinity should be limited to very small clusters which are connected by amorphous sections, and which have minimum chain folding. Such a form of UHMWPE should therefore better resist the shedding of fine polyethylene particles which currently processed conventional UHMWPE experiences under conditions of wear, e.g., under sliding friction in a joint.

This invention also includes the product made in accordance with the above described method.

Also provided in this invention is a method of making a prosthesis from UHMWPE so as to reduce production of fine particles from the prosthesis during wear of the prosthesis. UHMWPE having a polymeric structure with less than about 50% crystallinity, less than about 290 Å lamellar thickness and less than about 940 MPa tensile elastic modulus is provided. A prosthesis is formed from this UHMWPE, the UHMWPE forming a load bearing surface of the prosthesis. Formation of the prosthesis can be accomplished by standard procedures known to those skilled in the art, e.g., machining.

Also provided in this invention is a method of treating a body in need of a prosthesis. A shaped prosthesis formed of ultra high molecular weight polyethylene having a polymeric structure with less than about 50% crystallinity, less than about 290 Å lamellar thickness and less than about 940 MPa tensile elastic modulus, is provided. This prosthesis is applied to the body in need of the prosthesis. The prosthesis reduces production of fine particles from the prosthesis during wear of the prosthesis. In preferred embodiments, the ultra high molecular weight polyethylene forms a load bearing surface of the prosthesis.

The products and processes of this invention also apply to other polymeric materials such as high-density-polyethylene, low-density-polyethylene, linear-low-density-polyethylene and polypropylene.

The following non-limiting examples further illustrate the present invention.

EXAMPLES

Example 1

Method of Making Melt-Irradiated UHMWPE (MIR)

This example illustrates electron irradiation of melted UHMWPE.

A cuboidal specimen of size 10 mm×12 mm×60 mm, prepared from conventional ram extruded UHMWPE bar stock (GUR 415, obtained from Westlake Plastics, Lenni, Pa.) was placed in a chamber. The atmosphere within the chamber consisted of low oxygen nitrogen gas (<0.5 ppm oxygen gas) (obtained from AIRCO, Murray Hill, N.J.). The pressure in the chamber was approximately 1 atm. The temperature of the sample and the irradiation chamber was controlled using a heater, a variac and a thermocouple readout (manual) or temperature controller (automatic). The chamber was heated with a 270 W heating mantle. The chamber was heated (controlled by the variac) at a rate such that the steady state temperature of the sample was about 175° C. The sample was held at the steady state temperature for 30 minutes before starting the irradiation.

Irradiation was done using a van de Graaff generator with electrons of energy 2.5 MeV and a dose rate of 1.67 MRad/min. The sample was given a dose of 20 MRad with the electron beam hitting the sample on the 60 mm×12 mm surface. The heater was switched off after irradiation, and the sample was allowed to cool within the chamber under inert atmosphere, nitrogen gas, to 25° C. at approximately 0.5° C./minute. As a control, similar specimens were prepared using unheated and unirradiated bar stock of conventional UHMWPE.

Example 2

Comparison of Properties of GUR 415 UHMWPE Bar Stock and Melt-Irradiated (MIR) GUR 415 UHMWPE Bar Stock (20 MRad)

This example illustrates various properties of the irradiated and unirradiated samples of UHMWPE bar stock (GUR 415) obtained from Example 1. The tested samples were as follows: the test sample was bar stock which was molten and then irradiated while molten; control was bar stock (no heating/melting, no irradiation).

(A) Differential Scanning Calorimetry (DSC)

A Perkin-Elmer DSC7 was used with an ice-water heat sink and a heating and cooling rate of 10° C./minute with a continuous nitrogen purge. The crystallinity of the samples obtained from Example 1 was calculated from the weight of the sample and the heat of melting of polyethylene crystals (69.2 cal/g). The temperature corresponding to the peak of the endotherm was taken as the melting point. The lamellar thickness was calculated by assuming a lamellar crystalline morphology, and knowing the heat of crystallization (69.2 cal/g), the melting point of a perfect crystal (418.15 K), the density of the crystalline regions (1.005 g/cm$^3$) and the end free surface energy of polyethylene (2.22×10$^{-6}$ cal/cm$^2$). The results are shown in Table 1 and FIG. 4.

TABLE 1

| | DSC (10° C./min) | |
|---|---|---|
| Property | GUR 415 (unirradiated) 0 MRad | GUR 415 (melt-irradiated) 20 MRad |
| Crystallinity (%) | 50.2 | 37.8 |
| Melting Point (C.) | 135.8 | 125.5 |
| Lamellar thickness (Å) | 290 | 137 |

The results indicate that the melt-irradiated sample had a more entangled and less crystalline polymeric structure than the unirradiated sample, as evidenced by lower crystallinity, lower lamellar thickness and lower melting point.

(B) Swell Ratio

The samples were cut into cubes of size 2 mm×2 mm×2 mm and kept submerged in Decalin at 150° C. for a period of 24 hours. An antioxidant (1% N-phenyl-2-naphthylamine) was added to the Decalin to prevent degradation of the sample. The swell ratio and percent extract were calculated by measuring the weight of the sample before the experiment, after swelling for 24 hours and after vacuum drying the swollen sample. The results are shown in Table 2.

TABLE 2

| | Swelling in Decalin with Antioxidant for 24 hours at 150° C. | |
|---|---|---|
| Property | GUR 415 (unirradiated) 0 MRad | GUR 415 (melt-irradiated) 20 MRad |
| Swell Ratio | dissolves | 2.5 |
| Extract (%) | approx. 100% | 0.0 |

The results indicate that the melt-irradiated UHMWPE sample was highly crosslinked, and hence did not allow dissolution of polymer chains into the hot solvent even after 24 hours, while the unirradiated sample dissolved completely in the hot solvent in the same period.

(C) Tensile Elastic Modulus

ASTM 638 M III of the samples was followed. The strain was 1 mm/minute. The experiment was performed on a MTS machine. The results are shown in Table 3.

TABLE 3

| | Elastic Test (ASTM 638 M III, 1 mm/min. | |
|---|---|---|
| Property | GUR 415 (unirradiated) 0 MRad | GUR 415 (melt-irradiated) 20 MRad |
| Tensile Elastic modulus (MPa) | 940.7 | 200.8 |
| Yield stress (MPa) | 22.7 | 14.4 |

TABLE 3-continued

| | Elastic Test (ASTM 638 M III, 1 mm/min. | |
|---|---|---|
| Property | GUR 415 (unirradiated) 0 MRad | GUR 415 (melt-irradiated) 20 MRad |
| Strain at break (%) | 953.8 | 547.2 |
| Engineering UTS (MPa) | 46.4 | 15.4 |

The results indicate that the melt-irradiated UHMWPE sample had a significantly lower tensile elastic modulus than the unirradiated control. The lower strain at break of the melt-irradiated UHMWPE sample is yet further evidence for the crosslinking of chains in that sample.

(D) Hardness

The hardness of the samples was measured using a durometer on the shore D scale. The hardness was recorded for instantaneous indentation. The results are shown in Table 4.

TABLE 4

| | Hardness (Shore D) | |
|---|---|---|
| Property | GUR 415 (unirradiated) 0 MRad | GUR 415 (melt-irradiated) 20 MRad |
| Hardness (D Scale) | 65.5 | 54.5 |

The results indicate that the melt-irradiated UHMWPE was softer than the unirradiated control.

(E) Light Transmissivity (transparency)

Transparency of the samples was measured as follows: Light transmission was studied for a light of wave length 517 nm passing through a sample of approximately 1 mm in thickness placed between two glass slides. The samples were prepared by polishing the surfaces against 600 grit paper. Silicone oil was spread on the surfaces of the sample and then the sample was placed in between two slides. The silicone oil was used in order to reduce diffuse light scattering due to the surface roughness of the polymer sample. The reference used for this purpose was two similar glass slides separated by a thin film of silicone oil. The transmissivity was measured using a Perkin Elmer Lambda 3B uv-vis spectrophotometer. The absorption coefficient and transmissivity of a sample exactly 1 mm thick were calculated using the Lambert-Beer law. The results are shown in Table 5.

TABLE 5

| | Transmissivity of Light at 517 nm | |
|---|---|---|
| Property | GUR 415 (unirradiated) 0 MRad | GUR 415 (melt-irradiated) 20 MRad |
| Transmission (%) (1 mm sample) | 8.59 | 39.9 |
| Absorption coefficient (cm$^1$) | 24.54 | 9.18 |

The results indicate that the melt-irradiated UHMWPE sample transmitted much more light through it than the control, and hence is much more transparent than the control.

(F) Environmental Scanning Electron Microscopy (ESEM)

ESEM (ElectroScan, Model 3) was performed on the samples at 10 kV (low voltage to reduce radiation damage to the sample) with an extremely thin gold coating (approximately 20 Å to enhance picture quality). By studying the surface of the polymer under the ESEM with and without the gold coating, it was verified that the thin gold coating did not produce any artifacts.

The samples were etched using a permanganate etch with a 1:1 sulfuric acid to orthophosphoric acid ratio and a 0.7% (w/v) concentration of potassium permanganate before being viewed under the ESEM.

Figure 4:
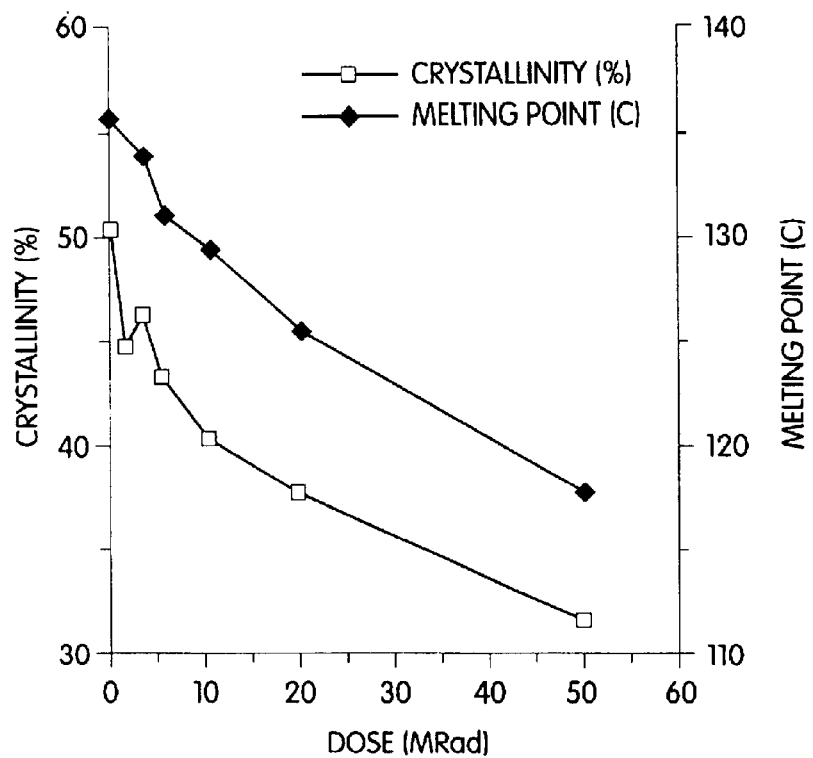
FIG. 4 is a graph showing the crystallinity and melting point of melt-irradiated UHMWPE at different irradiation doses.
Figure 5:
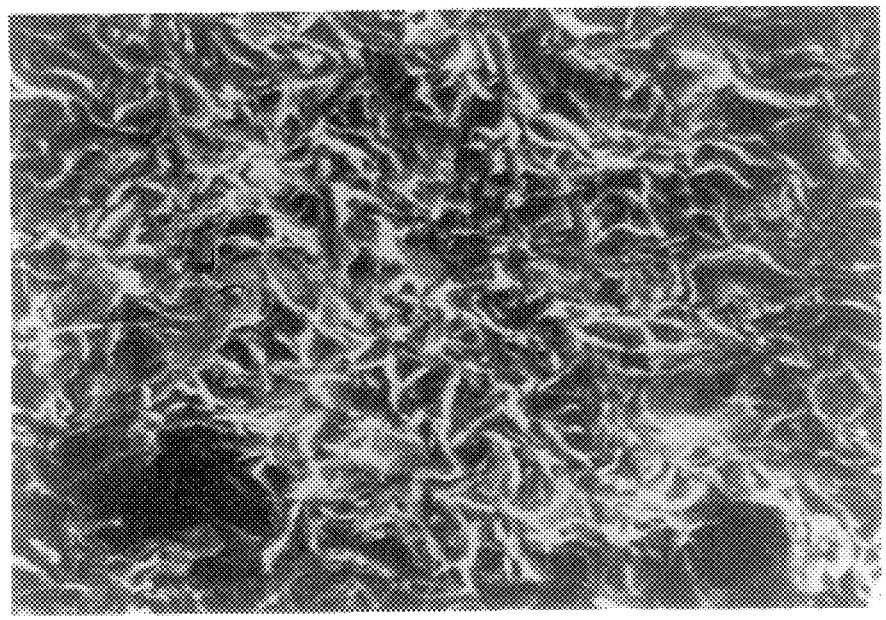
FIG. 5 is an environmental scanning electron micrograph of an etched surface of conventional UHMWPE showing its crystalline structure.
Figure 6:
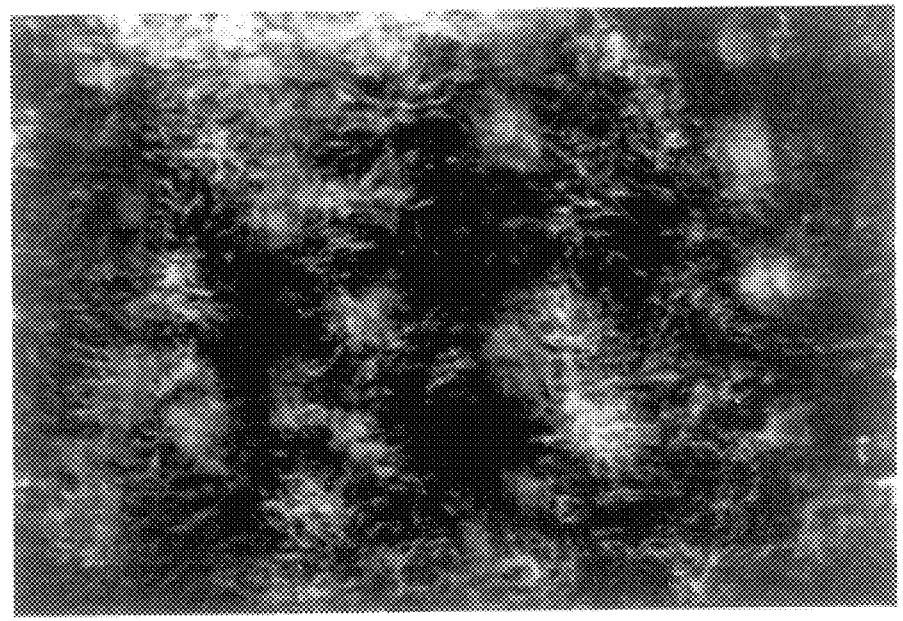
FIG. 6 is an environmental scanning electron micrograph of an etched surface of melt-irradiated UHMWPE showing its crystalline structure at approximately the same magnification as in FIG. 5.

FIG. 4 shows an ESEM (magnification of 10,000×) of an etched surface of conventional UHMWPE (GUR 415; unheated; unirradiated). FIG. 5 shows an ESEM (magnification of 10,500×) of an etched surface of melt-irradiated UHMWPE (GUR 415; melted; 20 MRad). The ESEMs indicated a reduction in size of the crystallites and the occurrence of imperfect crystallization in the melt-irradiated UHMWPE as compared to the conventional UHMWPE.

(G) Fourier Transform Infra Red Spectroscopy (FTIR)

FTIR of the samples was performed using a microsampler on the samples rinsed with hexane to remove surface impurities. The peaks observed around 1740 to 1700 $cm^{-1}$ are bands associated with oxygen containing groups. Hence, the ratio of the area under the carbonyl peak at 1740 $cm^{-1}$ to the area under the methylene peak at 1460 $cm^{-1}$ is a measure of the degree of oxidation.

The FTIR spectra indicate that the melt-irradiated UHMWPE sample showed more oxidation than the conventional unirradiated UHMWPE control, but a lot less oxidation than an UHMWPE sample irradiated in air at room temperature and given the same irradiation dose as the melt-irradiated sample.

(H) Electron Paramagnetic Resonance (EPR)

EPR was performed at room temperature on the samples which were placed in a nitrogen atmosphere in an air tight quartz tube. The instrument used was the Bruker ESP 300 EPR spectrometer and the tubes used were Taperlok EPR sample tubes obtained from Wilmad Glass Company, Buena, N.J.

The unirradiated samples do not have any free radicals in them since irradiation is the process which creates free radicals in the polymer. On irradiation, free radicals are created which can last for several years under the appropriate conditions.

The EPR results indicate that the melt-irradiated sample did not show any free radicals when studied using an EPR immediately after irradiation, whereas the sample which was irradiated at room temperature under nitrogen atmosphere showed trans-vinylene free radicals even after 266 days of storage at room temperature. The absence of free radicals in the melt-irradiated UHMWPE sample means that any further oxidative degradation was not possible.

(I) Wear

The wear resistance of the samples was measured using a bi-axial pin-on-disk wear tester. The wear test involved the rubbing action of UHMWPE pins (diameter=9 mm; height= 13 mm) against a Co—Cr alloy disk. These tests were carried out to a total of 2 million cycles. The unirradiated pin displayed a wear rate of 8 mg/million cycles while the irradiated pin had a wear rate of 0.5 mg/million cycles. The results indicate that the melt-irradiated UHMWPE has far superior wear resistance than the unirradiated control.

Example 3

Method of Making Melt-Irradiated (MIR) UHMWPE Conventional Articular Cups

This example illustrates electron irradiation of a melted UHMWPE conventional articular cup.

A conventional articular cup (high conformity unsterilized UHMWPE cup made by Zimmer, Inc., Warsaw, Ind.) of internal diameter 26 mm and made of GUR 415 ram extruded bar stock, was irradiated under controlled atmosphere and temperature conditions in an air-tight chamber with a titanium cup holder at the base and a thin stainless steel foil (0.001 inches thick) at the top. The atmosphere within this chamber consisted of low oxygen nitrogen gas (<0.5 ppm oxygen gas) (obtained from AIRCO, Murray Hill, N.H.). The pressure in the chamber was approximately 1 atm. The chamber was heated using a 270 W heating mantle at the base of the chamber which was controlled using a temperature controller and a variac. The chamber was heated such that the temperature at the top surface of the cup rose at approximately 1.5° to 2° C./min, finally asymptotically reaching a steady state temperature of approximately 175° C. Due to the thickness of the sample cup and the particular design of the equipment used, the steady state temperature of the cup varied between 200° C. at the base to 175° C. at the top. The cup was held at these temperatures for a period of 30 minutes before starting the irradiation.

Irradiation was done using a van de Graaff generator with electrons of energy 2.5 MeV and a dose rate of 1.67 MRad/min. The beam entered the chamber through the thin foil at top and hit the concave surface of the cup. The dose received by the cup was such that a maximum dose of 20 MRad was received approximately 5 mm below the surface of the cup being hit by the electrons. After irradiation, the heating was stopped and the cup was allowed to cool to room temperature (approximately 25° C.) while still in the chamber with nitrogen gas. The rate of cooling was approximately 0.5° C./min. The sample was removed from the chamber after the chamber and the sample had reached room temperature.

The above irradiated cup which increases in volume (due to the decrease in density accompanying the reduction of crystallinity following melt-irradiation) can be remachined to the appropriate dimensions.

Example 4

Swell Ratio and Percent Extract at Different Depths for Melt-Irradiated (MIR) UHMWPE Articular Cups This example illustrates the swell ratio and percent extract at different depths of the melt-irradiated articular cup obtained from Example 3. Samples of size 2 mm×2 mm×2 mm were cut from the cup at various depths along the axis of the cup. These samples were then kept submerged in Decalin at 150° C. for a period of 24 hours. An antioxidant (1% N-phenyl-2-naphthylamine) was added to the Decalin to prevent degradation of the sample. The swell ratio and percent extract were calculated by measuring the weight of the sample before the experiment, after swelling for 24 hours, and after vacuum drying the swollen sample. The results are shown in Table 6.

TABLE 6

The Swell Ratio and Percent Extract at Different Depths on the Melt-Irradiated UHMWPE Articular Cup

| Depth (mm) | Swell Ratio (Decalin, 150° C., 1 day) | % Extract |
|---|---|---|
| 0–2 | 2.43 | 0.0 |
| 2–4 | 2.52 | 0.0 |
| 4–6 | 2.51 | 0.0 |
| 6–8 | 2.64 | 0.0 |
| 8–10 | 2.49 | 0.0 |
| 10–12 | 3.68 | 0.0 |
| >12 | 6.19 | 35.8 |
| Unirradiated | Dissolves | Approx. 100% |

The results indicate that the UHMWPE in the cup had been crosslinked to a depth of 12 mm due to the melt-irradiation process to such an extent that no polymer chains dissolved out in hot Decalin over 24 hours.

Example 5

Crystallinity and Melting Point at Different Depths for the Melt-Irradiated (MIR) UHMWPE Articular Cups This example illustrates the crystallinity and melting point at different depths of the melt-irradiated cup obtained from Example 3.

Samples were taken from the cup at various depths along the axis of the cup. The crystallinity is the fraction of the polymer that is crystalline. The crystallinity was calculated by knowing the weight of the sample (w, in g), the heat absorbed by the sample in melting (E, in cal which was measured experimentally using a Differential Scanning Calorimeter at 10° C./min) and the heat of melting of polyethylene crystals ($\Delta H = 69.2$ cal/g), using the following equation:

$$\% \text{ crystallinity} = \frac{E}{w \cdot \Delta H}$$

Figure 7:
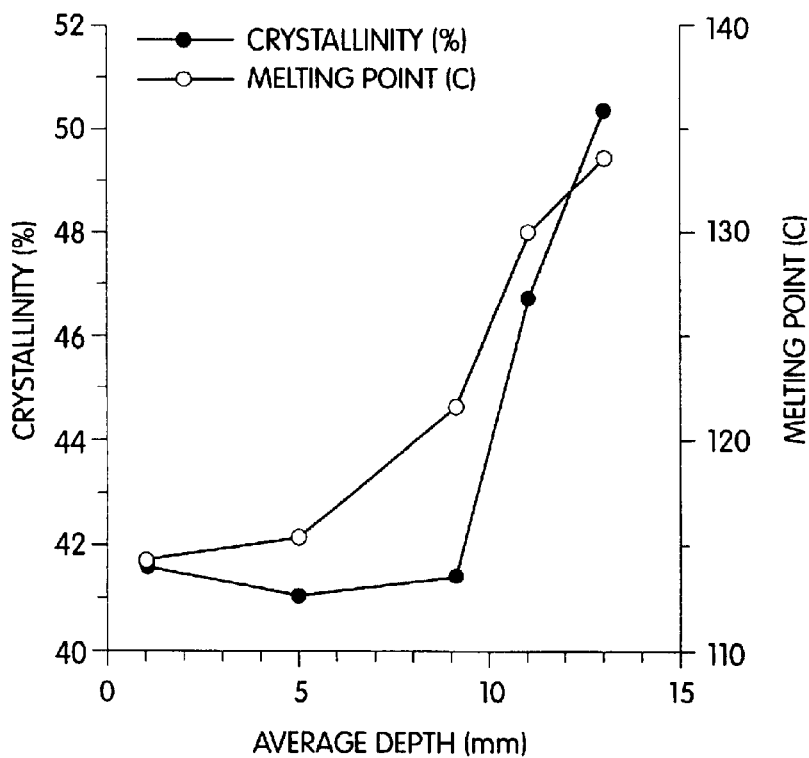
FIG. 7 is a graph showing the crystallinity and melting point at different depths of a melt-irradiated UHMWPE cup.

The melting point is the temperature corresponding to the peak in the DSC endotherm. The results are shown in FIG. 7.

The results indicate that the crystallinity and the melting point of the melt-irradiated UHMWPE in the articular cups obtained from Example 3 were much lower than the corresponding values of the conventional UHMWPE, even to a depth of 1 cm (the thickness of the cup being 1.2 cms).

Example 6

Second Method of Making Melt-Irradiated (MIR) UHMWPE Articular Cups

This example illustrates a method for making articular cups with melt-irradiated UHMWPE.

Conventional UHMWPE bar stock made from GUR 415 (obtained from West Lake Plastics, Lenni, Pa.) was machined to the shape of a cylinder, of height 4 cm and diameter 5.2 cm. One circular face of the cylinder was machined to include an exact hemispherical hole, of diameter 2.6 cm, such that the axis of the hole and the cylinder coincided. This specimen was enclosed in an air-tight chamber with a thin stainless steel foil (0.001 inches thick) at the top. The cylindrical specimen was placed such that the hemispherical hole faced the foil. The chamber was then flushed and filled with an atmosphere of low oxygen nitrogen gas (<0.5 ppm oxygen gas) obtained from AIRCO, Murray Hill, N.J.). Following this flushing and filling, a slow continuous flow of nitrogen was maintained while keeping the pressure in the chamber at approximately 1 atm. The chamber was heated using a 270 W heating mantle at the base of the chamber which was controlled using a temperature controller and a variac. The chamber was heated such that the temperature at the top surface of the cylindrical specimen rose at approximately 1.5° C. to 2° C./min, finally asymptomatically reaching a steady state temperature of approximately 175° C. The specimen was then held at this temperature for a period of 30 minutes before starting irradiation.

Irradiation was done using a van de Graaff generator with electrons of energy 2.5 MeV and a dose rate of 1.67 MRad/min. The beam entered the chamber through the thin foil at top and hit the surface with the hemispherical hole. The dose received by the specimen was such that a maximum dose of 20 MRad was received approximately 5 mm below the surface of the polymer being hit by the electrons. After irradiation, the heating was stopped and the specimen was allowed to cool to room temperature (approximately 25° C.) while still in the chamber with nitrogen gas. The rate of cooling was approximately 0.5° C./min. The sample was removed from the chamber after the chamber and the sample had reached room temperature.

This cylindrical specimen was then machined into an articular cup with the dimensions of a high conformity UHMWPE articular cup of internal diameter 26 mm manufactured by Zimmer, Inc., Warsaw, Ind., such that the concave surface of the hemispherical hole was remachined into the articulating surface. This method allows for the possibility of relatively large changes in dimensions during melt irradiation.

Example 7

Electron Irradiation of UHMWPE Pucks

This example illustrates that electron irradiation of UHMWPE pucks gives a non-uniform absorbed dose profile.

UHMWPE bar stock made from GUR 415 resin (obtained from Westlake Plastics, Lenni, Pa.) was used. This resin has a molecular weight of 5,000,000 g/mol and contains 500 ppm of calcium stearate. The bar stock was obtained by the ram extrusion of the powder resin. The bar stock was cut into "hockey puck" shaped cylinders (height 4 cm, diameter 8.5 cm).

The pucks were irradiated with an electron-beam incident to one of the circular bases of the pucks with a linear electron accelerator operated at 10 MeV and 1 kW (AECL, Manitoba Canada). Due to a cascade effect, electron beam irradiation results in a non-uniform absorbed dose profile. Table 7. illustrates the calculated absorbed dose values at various depths in a specimen of polyethylene irradiated with 10

MeV electrons. The absorbed doses were the values measured at the top surface (surface of e-beam incidence).

TABLE 7

The variation of absorbed dose as a function of depth in polyethylene

| Depth (mm) | Absorbed Dose (Mrad) |
|---|---|
| 0 | 20 |
| 0.5 | 22 |
| 1.0 | 23 |
| 1.5 | 24 |
| 2.0 | 25 |
| 2.5 | 27 |
| 3.0 | 26 |
| 3.5 | 23 |
| 4.0 | 20 |
| 4.5 | 8 |
| 5.0 | 3 |
| 5.5 | 1 |
| 6.0 | 0 |

Example 8

Method of Making UHMWPE Using Cold Irradiation and Subsequent Irradiation Melting (CIR-SM)

This example illustrates a method of making UHMWPE that has a cross-linked structure and has substantially no detectable free radicals, by cold irradiating and then melting the UHMWPE.

The pucks described in Example 7 were irradiated at room temperature at a dose rate of 2.5 Mrad per pass to 2.5, 5, 7.5, 10, 12.5, 15, 17.5, 20, 30, and 50 Mrad total absorbed dose as measured on the top surface (e-beam incidence). The pucks were not packaged and the irradiation was carried out in air. Subsequent to irradiation, the pucks were heated to 150° C. under vacuum for 2 hours so as to melt the polymer and thereby result in the recombination of free radicals leading to substantially no detectable residual free radicals.

The residual free radicals are measured by electron paramagnetic resonance as described in Jahan et al., J. Biomedical Materials Research 25:1005 (1991). The pucks were then cooled to room temperature at a rate of 5° C./min.

Example 9

Method of Making UHMWPE Using Warm Irradiation and Subsequent Irradiation Melting (WIR-SM)

This example illustrates a method of making UHMWPE that has a cross-linked structure and has substantially no detectable free radicals, by irradiating UHMWPE that has been heated to below the melting point and then melting the UHMWPE.

The pucks described in Example 7 are heated to 100° C. in air in an oven. The heated pucks are then irradiated with an electron beam to a total dose of 20 Mrad at a dose rate of 2.5 Mrad per pass. Subsequent to irradiation, the pucks are heated to 150° C. under vacuum for 2 hours, thereby allowing the free radicals to recombine leading to substantially no detectable residual free radicals. The pucks are then cooled to room temperature at a rate of 5° C./min.

Example 10

Method of Making UHMWPE Using Warm Irradiation and Adiabatic Melting (WIR-AM)

This example illustrates a method of making UHMWPE that has a cross-linked structure and has substantially no detectable free radicals, by irradiating UHMWPE that has been heated to below the melting point so as to generate adiabatic melting of the UHMWPE.

Two pucks as described in Example 7 were packed in a fiberglass pouch (obtained from Fisher Scientific Co., Pittsburgh, Pa.) to minimize heat loss in subsequent processing steps. First, the wrapped pucks were heated overnight in an air convection oven kept at 120° C. As soon as the pucks were removed from the oven they were placed under an electron-beam as described in Example 7 and immediately irradiated to 21 and 22.5 Mrad, respectively. Following the irradiation, the pucks were cooled to room temperature at a rate of 5° C./minute, at which point the fiberglass pouch was removed and the specimens analyzed.

Example 11

Comparison of Properties of GUR 415 UHMWPE Bar Stock Pucks and CIR-SM and WIR-AM-Treated Bar Stock Pucks This example illustrates various properties of the irradiated and unirradiated samples of UHMWPE bar stock GUR 415 obtained from Examples 8 and 10. The tested samples were as follows: (i) test samples (pucks) from bar stock which was irradiated at room temperature, subsequently heated to about 150° C. for complete melting of polyethylene crystals, followed by cooling to room temperature (CIR-SM), (ii) test samples (pucks) from bar stock which was heated to 120° C. in a fiberglass pouch so as to minimize heat loss from the pucks, followed by immediate irradiation to generate adiabatic melting of the polyethylene crystals (WIR-AM), and (iii) control bar stock (no heating/melting, no irradiation).

A. Fourier Transform Infra Red Spectroscopy (FTIR)

Infra-red (IR) spectroscopy of the samples was performed using a BioRad UMA 500 infrared microscope on thin sections of the samples obtained from Examples 8 and 10. The thin sections (50 $\mu$m) were prepared with a sledge microtome. The IR spectra were collected at 20 $\mu$m, 100 $\mu$m, and 3 mm below the irradiated surface of the pucks with an aperture size of 10×50 $\mu m^2$. The peaks observed around 1740 to 1700 $cm^{-1}$ are associated with the oxygen containing groups. Hence, the ratio of the area under the carbonyl peak at 1740 $cm^{-1}$ to the area under the methylene peak at 1460 $cm^{-1}$, after subtracting the corresponding baselines, was a measure of the degree of oxidation. Tables 8 and 9 summarize the degree of oxidation for the specimens described in Examples 8 and 10.

This data shows that following the cross-linking procedures there was some oxidation within a skin layer of about 100 $\mu$m thickness. Upon machining this layer away, the final product would have the same oxidation levels as the unirradiated control.

TABLE 8

Degree of oxidation of specimens from Example 8 (CIR-SM) (with post-irradiation melting in vacuum)

| Specimen | Oxidation Degree at various depths (A. U.) | | |
|---|---|---|---|
| | 20 $\mu$m | 100 $\mu$m | 3 mm |
| Unirradiated Control | 0.01 | 0.01 | 0.02 |
| Irradiated to 2.5 Mrad | 0.04 | 0.03 | 0.03 |
| Irradiated to 5 Mrad | 0.04 | 0.03 | 0.01 |

TABLE 8-continued

Degree of oxidation of specimens from Example 8
(CIR-SM) (with post-irradiation melting in vacuum)

| Specimen | Oxidation Degree at various depths (A. U.) | | |
|---|---|---|---|
| | 20 μm | 100 μm | 3 mm |
| Irradiated to 7.5 Mrad | 0.05 | 0.02 | 0.02 |
| Irradiated to 10 Mrad | 0.02 | 0.03 | 0.01 |
| Irradiated to 12.5 Mrad | 0.04 | 0.03 | 0.01 |
| Irradiated to 15 Mrad | 0.03 | 0.01 | 0.02 |
| Irradiated to 17.5 Mrad | 0.07 | 0.05 | 0.02 |
| Irradiated to 20 Mrad | 0.03 | 0.02 | 0.01 |

TABLE 9

Degree of oxidation of specimens from Example 10 (WIR-AM)

| Specimen | Oxidation Degree at (A. U.) | | |
|---|---|---|---|
| | 20 μm | 100 μm | 3 mm |
| Unirradiated Control | 0.01 | 0.01 | 0.02 |
| Irradiated to 15 Mrad | 0.02 | 0.01 | 0.03 |
| Irradiated to 16 Mrad | 0.02 | 0.02 | 0.01 |

B. Differential Scanning Calorimetry (DSC)

A Perkin-Elmer DSC7 was used with an ice-water heat sink and a heating and cooling rate of 10 C./minute with a continuous nitrogen purge. The crystallinity of the specimens obtained from Examples 8 and 10 was calculated from the weight of the sample and the heat of melting of polyethylene crystals measured during the first heating cycle. The percent crystallinity is given by the following equation:

$$\% \text{ crystallinity} = \frac{E}{w\Delta H}$$

where E and w are the heat of melting (in Joules) and weight (in gram) of the specimen tested, respectively, and $\Delta H$ is the heat of melting of 100% crystalline polyethylene in Joules/gram (291 J/g). The temperature corresponding to the peak of the endotherm was taken as the melting point. In some cases where there were multiple endotherm peaks, multiple melting points corresponding to these endotherm peaks have been reported. The crystallinities and melting points for the specimens described in Examples 8 and 10 are reported in Tables 10 and 11.

TABLE 10

DSC at a heating rate of 10° C./min
for specimens of Example 8 (CIR-SM)

| Specimen | Crystallinity (%) | Melting Point (° C.) |
|---|---|---|
| Unirradiated Control | 59 | 137 |
| Irradiated to 2.5 Mrad | 54 | 137 |
| Irradiated to 5 Mrad | 53 | 137 |
| Irradiated to 10 Mrad | 54 | 137 |
| Irradiated to 20 Mrad | 51 | 137 |
| Irradiated to 30 Mrad | 37 | 137 |

TABLE 11

DSC at a heating rate of 10° C./min
for specimens of Example 10 (WIR-SM)

| Specimen | Crystallinity (%) | Melting Point (° C.) |
|---|---|---|
| Unirradiated Control | 59 | 137 |
| Irradiated to 21 Mrad | 54 | 120–135–145 |
| Irradiated to 22.5 Mrad | 48 | 120–135–145 |

The data shows that the crystallinity dose not changes signficantly up to absorbed doses of 20 Mrad. Therefore, the elastic properties of the cross-linked material should remain unchanged upon cross-linking. On the other hand, one could tailor the elastic properties by changing the crystallinity with higher doses.

C. Pin-on-Disc Experiments for Wear Rate

The pin-on-disc (POD) experiments were carried out on a bi-axial pin-on-disc tester at a frequency of 2 Hz where polymeric pins were tested by a rubbing action of the pin against a highly polished Co—Cr disc. Prior to preparing cylindrical shaped pins (height 13 mm, diameter 9 mm), one millimeter from the surface of the pucks was machined away in order to remove the outer layer that had been oxidized during irradiation and post- and pre-processing. The pins were then machined from the core of the pucks and tested on the POD such that the surface of e-beam incidence was facing the Co—Cr disc. The wear tests were carried out to a total of 2,000,000 cycles in bovine serum. The pins were weighed at every 500,000 cycle and the average values of weight loss (wear rate) are reported in Tables 12 and 13 for specimens obtained from Examples 8 and 10 respectively.

TABLE 12

POD wear rates for specimens of Example 8 (CIR-SM)

| Specimen | Wear Rate (mg/million cycle) |
|---|---|
| Unirradiated Control | 9.78 |
| Irradiated to 20 Mrad | 0.22 |

TABLE 13

POD wear rates for specimens of Example 10 (WIR-AM)

| Specimen | Wear Rate (mg/million cycle) |
|---|---|
| Unirradiated Control | 9.78 |
| Irradiated to 21 Mrad | 1.15 |

The results indicate that the cross-linked UHMWPE has far superior wear resistance than the unirradiated control.

D. Gel Content and Swell Ratio

The samples were cut in cubes of size 2×2×2 mm³ and kept submerged in xylene at 130° C. for a period of 24 hours. An antioxidant (1% N-phenyl-2-naphthylamine) was added to the xylene to prevent degradation of the sample. The swell ratio and gel content were calculated by measuring the weight of the sample before the experiment, after swelling for 24 hours and after vacuum drying the swollen sample. The results are shown in Tables 14 and 15 for the specimens obtained from the Examples 8 and 10.

TABLE 14

Gel content and swell ratio for specimens of Example 8 (CIR-SM)

| Specimen | Gel Content (%) | Swell Ratio |
| --- | --- | --- |
| Unirradiated Control | 89.7 | 12.25 |
| Irradiated to 5 Mrad | 99.2 | 4.64 |
| Irradiated to 10 Mrad | 99.9 | 2.48 |
| Irradiated to 20 Mrad | 99.0 | 2.12 |
| Irradiated to 30 Mrad | 99.9 | 2.06 |

TABLE 15

Gel content and swell ratio for specimens of Example 10 (WIR-SM)

| Specimen | Gel Content (%) | Swell Ratio |
| --- | --- | --- |
| Unirradiated Control | 89.7 | 12.25 |
| Irradiated to 21 Mrad | 99.9 | 2.84 |
| Irradiated to 22.5 Mrad | 100 | 2.36 |

The results show that the swell ratio decreased with increasing absorbed dose indicating an increase in the cross-link density. The gel content increased indicating the formation of a cross-linked structure.

Example 12

Crystallinity and Melting Point at Different Depths for UHMWPE Prepared by Cold Irradiation and Post-Irradiation Melting (CIR-SM)

This example illustrates the crystallinity and melting point at different depths of the cross-linked UHMWPE specimens obtained from Example 8 with 20 Mrad total radiation dose. Samples were taken at various depths from the cross-linked specimen. The crystallinity and the melting point were determined using a Perkin Elmer differential scanning calorimeter as described in Example 10(B). The results are shown in Table 16.

TABLE 16

DSC at a heating rate of 10° C./min for specimen of Example 8 irradiated to a total dose of 20 Mrad (CIR-SM)

| Depth (mm) | Crystallinity (%) | Melting Point (° C.) |
| --- | --- | --- |
| 0–2 | 53 | 137 |
| 6–8 | 54 | 137 |
| 9–11 | 54 | 137 |
| 14–16 | 34 | 137 |
| 20–22 | 52 | 137 |
| 26–28 | 56 | 137 |
| 29–31 | 52 | 137 |
| 37–40 | 54 | 137 |
| Unirradiated Control | 59 | 137 |

The results indicate that the crystallinity varied as a function of depth away from the surface. The sudden drop in 16 mm is the consequence of the cascade effect. The peak in the absorbed dose was located around 16 mm where the dose level could be as high as 27 Mrad.

Example 13

Comparison of UHMWPE Prepared by CIR-SM Using Melting in Air Versus Melting Under Vacuum This example illustrates that the oxidation levels of UHMWPE pucks prepared by CIR-SM, whether melted in air or under vacuum, are the same as unirradiated pucks at a depth of 3 mm below the surface of the pucks.

Two pucks as described in Example 7 were irradiated at room temperature with a dose rate of 2.5 Mrad per pass to 17.5 Mrad total absorbed dose as measured on the top surface (e-beam incidence). The pucks were not packaged and the irradiation was carried out in air. Subsequent to irradiation, one puck was heated under vacuum to 150° C. for 2 hours, and the other puck was heated in air to 150° C. for 2 hours, so as to attain a state of no detectable residual crystalline content and no detectable residual free radicals. The pucks were then cooled to room temperature at a rate of 5° C./min. The pucks were then analyzed for the degree of oxidation as described in Example 10(A). Table 17 summarizes the results obtained for the degree of oxidation.

TABLE 17

Degree of oxidation of specimens melted in air versus in vacuum

| Specimen | Post-Melting Environment | Oxidation Degree at various depths (A. U.) | | |
| --- | --- | --- | --- | --- |
| | | 20 μm | 100 μm | 3 3 mm |
| Unirradiated Control | N/A | 0.01 | 0.01 | 0.02 |
| Irradiated to 17.5 Mrad | Vacuum | 0.07 | 0.05 | 0.02 |
| Irradiated to 17.5 Mrad | Air | 0.15 | 0.10 | 0.01 |

The results indicated that within 3 mm below the free surfaces the oxidation level in the irradiated UHMWPE specimens dropped to oxidation levels observed in unirradiated control UHMWPE. This was the case independent of post-irradiation melting atmosphere (air or vacuum). Therefore, post-irradiation melting could be done in an air convection oven without oxidizing the core of the irradiated puck.

Example 14

Method of Making UHMWPE Using Cold Irradiation and Subsequent Irradiation Melting Using Gamma Irradiation (CIR-SM)

This example, illustrates a method of making UHMWPE that has a cross-linked structure and has substantially no detectable free radicals, by cold irradiating with gamma-radiation and then melting the UHMWPE.

The pucks described in Example 7 were irradiated at room temperature at a dose rate of 0.05 Mrad/minute to 4 Mrad total absorbed dose as measured on the top surface (gamma ray incidence). The pucks were not packaged and irradiation was carried out in air. Subsequent to irradiation, the pucks were heated to 150° C. under vacuum for 2 hours so as to melt the polymer and thereby result in the recombination of free radicals leading to substantially no detectable residual free radicals.

Those skilled in the art will be able to ascertain using no more than routine experimentation, many equivalents of the specific embodiments of the invention described herein. These and all other equivalents are intended to be encompassed by the following claims.

What is claimed is:

1. A medical prosthesis for use within the body, said prosthesis being formed of ultra high molecular weight polyethylene, which has been radiation treated and melted such that the ultra high molecular weight polyethylene has substantially no detectable free radicals.

2. The prosthesis of claim 1 wherein said radiation is selected from the group consisting of gamma radiation and electron radiation.

3. The prosthesis of claim 1 wherein said ultra high molecular weight polyethylene has a cross-linked structure, so as to reduce production of particles from said prosthesis during wear of said prosthesis.

4. The prosthesis of claim 1 wherein said ultra high molecular weight polyethylene is substantially not oxidized.

5. The prosthesis of claim 1 wherein said ultra high molecular weight polyethylene is substantially oxidation resistant.

6. The prosthesis of claim 1 wherein said ultra high molecular weight polyethylene has substantially no chain scission.

7. The prosthesis of claim 1, wherein the ultra high molecular weight polyethylene (UHMWPE) has cross-linking so that a portion of said UHMWPE does not dissolve in xylene at 130° C. or DECALIN at 150° C. over a period of 24 hours.

8. The prosthesis of claim 1 wherein said ultra high molecular weight polyethylene has an initial average molecular weight of greater than about 2 million.

9. The prosthesis of claim 1 wherein part of said prosthesis is in the form of a cup or tray shaped article having a load bearing surface.

10. The prosthesis of claim 9 wherein said load bearing surface is in contact with a second part of said prosthesis having a mating load bearing surface of a metallic or ceramic material.

11. The prosthesis of claim 1 wherein said prosthesis is constructed and arranged for replacement of a joint selected from the group consisting of a hip joint, a knee joint, an elbow joint, a shoulder joint, an ankle joint and a finger joint.

12. A method for making a cross-linked ultra high molecular weight polyethylene (UHMWPE) having substantially no detectable free radicals, comprising the steps of:

providing conventional UHMWPE having polymeric chains wherein said UHMWPE is a cup or tray shaped article for use in a prosthesis;

irradiating said UHMWPE so as to cross-link said polymeric chains;

heating said irradiated UHMWPE above the melting temperature of said UHMWPE so that there are substantially no detectable free radicals in said UHMWPE; and cooling said heated UHMWPE to room temperature.

13. A method of making a medical prosthesis from ultra high molecular weight polyethylene which has been radiation treated and melted such that the ultra high molecular weight polyethylene has substantially no detectable free radicals, wherein said prosthesis results in the reduced production of particles from said prosthesis during wear of said prosthesis, wherein the method comprises the steps of:

providing ultra high molecular weight polyethylene which has been radiation treated and melted such that the ultra high molecular weight polyethylene has substantially no detectable free radicals; and forming a medical prosthesis from said ultra high molecular weight polyethylene so as to reduce production of particles from said prosthesis during wear of said prosthesis, wherein said ultra high molecular weight polyethylene forms a load bearing surface of said prosthesis.

14. A method of treating a body in need of a medical prosthesis, comprising:

providing a shaped medical prosthesis formed of ultra high molecular weight polyethylene which has been radiation treated and melted such that the ultra high molecular weight polyethylene has substantially no detectable free radicals; and applying said prosthesis to said body in need of said prosthesis.

15. A medical prosthesis for use within a body, wherein the medical prosthesis comprises cross-linked ultra high molecular weight polyethylene (UHMWPE) prepared by irradiation and melting, wherein the cross-linked UHMWPE is oxidation resistant.

16. The medical prosthesis of claim 15, wherein the melting is caused by the irradiation.

* * * * *